United States Patent [19]

Audiau et al.

[11] Patent Number: 5,424,439

[45] Date of Patent: Jun. 13, 1995

[54] PROCESS FOR THE PREPARATION OF 2-AMINO-4-NITROBENZOTHIAZOLE DERIVATIVES AND INTERMEDIATES

[75] Inventors: François Audiau, Charenton le Pont; Patrick Jimonet, Villepreux; Serge Mignani, Chatenay Malabry, all of France

[73] Assignee: Rhone-Poulenc Rorer S.A., Antony Cedex, France

[21] Appl. No.: 244,389

[22] PCT Filed: Dec. 9, 1992

[86] PCT No.: PCT/FR92/01166

§ 371 Date: Jun. 13, 1994

§ 102(e) Date: Jun. 13, 1994

[87] PCT Pub. No.: WO93/12100

PCT Pub. Date: Jun. 24, 1993

[30] Foreign Application Priority Data

Dec. 13, 1991 [FR] France ................ 91 15487

[51] Int. Cl.⁶ ............... C07D 277/82; C07F 7/08
[52] U.S. Cl. ..................... 548/110; 548/164
[58] Field of Search ................. 548/110, 164

[56] References Cited

U.S. PATENT DOCUMENTS 5,236,940 8/1993 Audiav ..................... 514/367

FOREIGN PATENT DOCUMENTS 0374041 6/1990 European Pat. Off. .

OTHER PUBLICATIONS

Chemical Abstracts, vol. 118, No. 1, 4 Jan. 1993, Columbus, Ohio, abstract no. 6906b, S. Mignani et al.

*Primary Examiner*—Robert Gerstl
*Attorney, Agent, or Firm*—Morgan & Finnegan

[57] ABSTRACT

This invention relates to the process for the preparation of a method for preparing derivatives of formula (I),

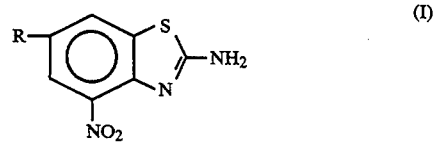

wherein R is an alkyl, alkoxy, alkylthio, polyfluoroalkyl, polyfluoroalkoxy, alkenyl, phenyl, alkylsulphonyl, alkoxycarbonyl, amino, cyano, sulphonamide or dialkylcarbamyl radical, characterized in that a derivative of formula (II),

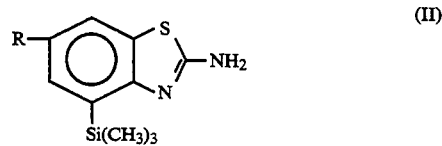

wherein R has the same meaning as in formula (I), is reacted with nitronium tetrafluoroborate and derivatives of formula (II).

9 Claims, No Drawings

PROCESS FOR THE PREPARATION OF 2-AMINO-4-NITROBENZOTHIAZOLE DERIVATIVES AND INTERMEDIATES

FIELD OF THE INVENTION

The present invention relates to a process for the preparation of 2-amino-4-nitrobenzothiazole derivatives of formula:

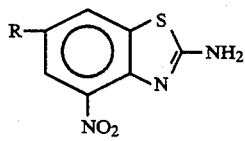

(I)

in which R denotes an alkyl, alkoxy, alkylthio, polyfluoroalkyl, polyfluoroalkoxy, alkenyl, phenyl, alkylsulphonyl, alkoxycarbonyl, amino, cyano, sulphonamide or dialkylcarbamoyl radical.

BACKGROUND OF THE INVENTION

From Patent EP 374041 it is known to prepare certain compounds of formula (I) by nitration, using nitric acid, of the corresponding 2-aminobenzothiazoles; however, these compounds are obtained mixed with the derivatives which are nitrated in position 5 and in very low yields. This process cannot therefore be applied industrially.

DESCRIPTION OF THE INVENTION

There has now been found, and it is this which forms the subject of the present application, anew process allowing the compounds of formula (I) to be obtained industrially and in good yields.

This process consists in reacting a derivative of formula:

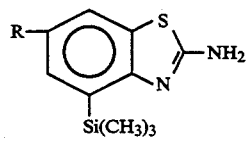

(II)

in which R has the same meanings as in formula (I) with nitronium tetrafluoroborate.

This reaction is performed in an inert organic solvent such as acetonitrile or tetramethylene sulphone.

It is particularly advantageous to operate at a temperature of between 10° C. and 30° C. and, preferably, at approximately 20° C.

The quantity of nitronium tetrafluoroborate is generally from 1 mole to 4 moles per one mole of derivative of formula (II). 2 moles of it are advantageously employed.

The reaction period is generally between 6 and 48 hours. It is generally 12 hours.

The derivatives of formula (II) are new and also form part of the invention.

The derivatives of formula (II) can be obtained by reaction of trimethylchlorosilane with the lithium derivatives of the corresponding 2-aminobenzothiazoles, the latter being obtained by the reaction of n-butyllithium with 2-aminobenzothiazoles.

This reaction is performed without isolation of the lithium derivative, in an inert solvent such as hexane, tetrahydrofuran or a mixture of these solvents, at a temperature close to −80° C.

2-Amino-4-bromobenzothiazoles can be obtained by bromination of the corresponding 2-aminobenzothiazoles.

This bromination is generally performed by means of bromine, in acetic acid, at a temperature of between 20° C. and 60° C.

2-Aminobenzothiazoles can be obtained by the method described by L. M. Yagupolskii et al., Zh. Obshch. Khim., 33 (7), 2301 (1963).

The compounds of formula (I) can be isolated from the reaction mixture by the usual techniques for isolation (for example extraction, chromatography, crystallization).

The derivatives of formula (I) can be employed as medications or intermediates for the preparation of medications (EP 282971 and EP 374041).

EXAMPLES

The example which follows shows how the invention may be used.

Example 1

0.68 g of nitronium tetrafluoroborate are added in small portions to a solution of 0.76 g of 2-amino-4-trimethylsilyl-6-trifluoromethoxybenzothiazole in 20 cm³ of acetonitrile cooled to 0° C. Stirring is continued for 12 hours at a temperature close to 20° C. The solution is then diluted with 50 cm³ of water and extracted with 2 times 50 cm³ of ethyl acetate. The organic phases are combined, dried over sodium sulphate and concentrated in vacuum. The residue is purified by flash chromatography on silica gel with a cyclohexane-ethyl acetate mixture (7–3 by volume) as eluent. After recrystallization from a cyclohexane-ethyl acetate mixture (3–2 by volume), 0.3 g of 2-amino-4-nitro-6-trifluoromethoxybenzothiazole melting at 260° C. is obtained.

2-Amino-4-trimethylsilyl-6-trifluoromethoxybenzothiazole can be prepared as follows: 18.7 cm³ of n-butyllithium (1.6M in hexane) are added dropwise over 1 hour to a solution of 3.13 g of 2-amino-4-bromo-6-trifluoromethoxybenzothiazole in 50 cm³ of tetrahydrofuran under nitrogen. The solution is stirred for 45 minutes at −78° C. and 6.5 g of trimethylchlorosilane are then added dropwise over 15 minutes. The mixture is stirred for 1 hour at 0° C., diluted with 100 cm³ of water and extracted with 2 times 100 cm³ of ethyl acetate. The organic phases are combined, dried over sodium sulphate and evaporated at reduced pressure. The residue is purified by flash chromatography on silica gel with a cyclohexane-ethyl acetate mixture (92–8 by volume) as eluent. After recrystallization from a dichloromethane-methanol mixture (95–5 by volume), 1.6 g of 2-amino-4-trimethylsilyl-6-trifluoromethylbenzothiazole melting at 76° C. are thus obtained.

2-Amino-4-bromo-6-trifluoromethoxybenzothiazole can be obtained as follows: 2.4 g of bromine in 6 cm³ of acetic acid are added dropwise, over 15 minutes, to a stirred solution of 3.51 g of 2-amino- 6-trifluoromethoxybenzothiazole in 30 cm³ of acetic acid at 50° C. The reaction mixture is stirred at 50° C. for 12 hours. After filtration and recrystallization from ethanol, 4.5 g of 2-amino-4-bromo-6-trifluoromethoxybenzothiazole hydrobromide melting at 300° C. are obtained.

2-Amino-6-trifluoromethoxybenzothiazole can be prepared by the method described by L. M. Yagupolskii et al., Zh. Obshch. Khim., 33 (7), 2301 (1963).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of derivatives of formula:

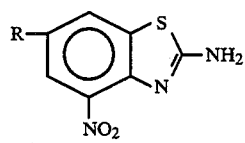 (I)

in which R denotes an alkyl, alkoxy, alkylthio, polyfluoroalkyl, polyfluoroalkoxy, alkenyl, phenyl, alkylsulphonyl, alkoxycarbonyl, amino, cyano, sulphonamide or dialkylcarbamoyl radical, comprising reacting a derivative of formula:

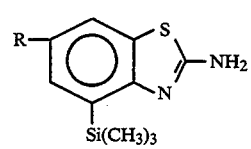 (II)

in which R has the same meanings as in formula (I) with nitronium tetrafluoroborate.

2. Process according to claim 1, wherein the reaction is carried out in an inert solvent.

3. Process according to claim 2, wherein the inert solvent is acetonitrile or tetramethylene sulphone.

4. Process according to claim 1, wherein the reaction is carried out at a temperature of between 10° and 30° C.

5. Process according to claim 4, wherein the reaction is carried out at a temperature of about 20° C.

6. Process according to claim 1, wherein 1 to 4 moles of nitronium tetrafluoroborate are employed per mole of derivative of formula (II).

7. Process according to claim 6, wherein 2 moles of nitronium tetrafluoroborate are employed.

8. Process according to claim 1, wherein the reaction period is between 6 and 48 hours.

9. Compounds of formula:

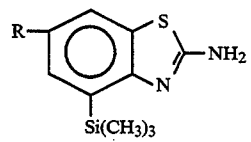 (II)

in which R denotes an alkyl, alkoxy, alkylthio, polyfluoroalkyl, polyfluoroalkoxy, alkenyl, phenyl, alkylsulphonyl, alkoxycarbonyl, amino, cyano, sulphonamide or dialkylcarbamoyl radical.

* * * * *